(12) United States Patent
Venkatesh et al.

(10) Patent No.: US 10,064,953 B2
(45) Date of Patent: Sep. 4, 2018

(54) DRUG DELIVERY SYSTEM AND METHOD

(71) Applicant: Auburn University, Auburn, AL (US)

(72) Inventors: Siddarth Venkatesh, Auburn, AL (US); Jacek Wower, Auburn, AL (US); Mark E. Byrne, Mullica Hill, NJ (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 14/955,309

(22) Filed: Dec. 1, 2015

(65) Prior Publication Data
US 2016/0082124 A1 Mar. 24, 2016

Related U.S. Application Data

(63) Continuation of application No. 11/985,263, filed on Nov. 13, 2007, now abandoned.

(60) Provisional application No. 60/937,773, filed on Jun. 28, 2007, provisional application No. 60/858,553, filed on Nov. 13, 2006.

(51) Int. Cl.
| | | |
|---|---|---|
| *A61K 47/48* | (2006.01) | |
| *A61K 31/70* | (2006.01) | |
| *A61K 48/00* | (2006.01) | |
| *C12N 15/87* | (2006.01) | |
| *A61K 47/34* | (2017.01) | |

(52) U.S. Cl.
CPC ........ *A61K 47/48784* (2013.01); *A61K 31/70* (2013.01); *A61K 47/48092* (2013.01); *A61K 47/48176* (2013.01); *A61K 47/48938* (2013.01); *A61K 47/48984* (2013.01); *A61K 48/0008* (2013.01); *A61K 48/0091* (2013.01); *C12N 15/87* (2013.01); *A61K 47/34* (2013.01)

(58) Field of Classification Search
None
See application file for complete search history.

(56) References Cited

U.S. PATENT DOCUMENTS

| | | | |
|---|---|---|---|
| 4,668,506 A | 5/1987 | Bawa | |
| 4,775,531 A | 10/1988 | Gilbard | |
| 4,911,933 A | 3/1990 | Gilbard | |
| 4,931,279 A | 6/1990 | Bawa et al. | |
| 5,318,780 A | 6/1994 | Viegas et al. | |
| 5,587,175 A | 12/1996 | Viegas et al. | |
| 5,840,338 A | 11/1998 | Roos et al. | |
| 5,876,709 A | 3/1999 | Itoh et al. | |
| 5,958,443 A | 9/1999 | Viegas et al. | |
| 6,136,334 A | 10/2000 | Viegas et al. | |
| 6,375,973 B2 | 4/2002 | Yanni et al. | |
| 6,552,103 B1 | 4/2003 | Bertozzi et al. | |
| 6,703,039 B2 | 3/2004 | Xia et al. | |
| 6,730,065 B1 | 5/2004 | Horn | |
| 6,735,470 B2 | 5/2004 | Henley et al. | |
| 7,332,586 B2 * | 2/2008 | Franzen ............... A61K 9/5115 424/491 |
| 2001/0006968 A1 | 7/2001 | Trimming et al. | |
| 2004/0096477 A1 | 5/2004 | Chauhan et al. | |
| 2005/0163844 A1 | 7/2005 | Ashton | |
| 2005/0208102 A1 | 9/2005 | Schultz | |
| 2006/0100408 A1 | 5/2006 | Powell et al. | |
| 2006/0177483 A1 | 8/2006 | Byrne et al. | |

OTHER PUBLICATIONS

Wang, et al. (Sep. 24, 2006 online) "Co-delivery of drugs and DNA from cationic core-shell nanoparticles self-assembled from a biodegradable copolymer", Nature Materials, 5: 791-96.*
Quigley, et al. (1980) "Molecular Structure of an anticancer drug-DNA complex: Daunomycin plus d(CpGpTpApCpG)", Proceedings of the National Academy of Science, USA., 77(12): 7204-08.*
Farokhzad 2004 "Nanoparticle-Aptamer Bioconjugates: A New Approach for Targeting Prostate Cancer Cells", Cancer Research, 64: 7668-72.*
Bagalkot, et al. (Nov. 13, 2006) "An Aptamer-Doxorubicin Physical Conjugate as a Novel Targeted Drug-Delivery Platform" Angewandte Chemie, 45: 8149-52.*
Alvarez-Lorenzo, et al., "Soft Contact Lenses Capable of Sustained Delivery of Timolol", Journal of Pharmaceutical Sciences, vol. 91, No. 10 (Oct. 2002), pp. 2182-2192. Oct. 31, 2002.
Berger, Eric, "In All the World How Many Diseases Have Humans Succeeded in Eradicating?", Internet Posting Oct. 20, 2010.
Byrne, Mark E., et al., "Molecular Imprinting Within Hydrogels", Advanced Drug Delivery Reviews, vol. 54 (2002), pp. 149-161. Aug. 25, 2001.
Byrne, Mark E., et al., "Networks for Recognition of Biomolecules: Molecular Imprinting and Micropatterning Poly(ethylene glycol)-Containing Films", Polymers for Advanced Technologies, vol. 13, (2002), pp. 798-816. May 1, 2002.
Hilt, J. Zachary, et al., "Configurational Biomimesis in Drug Delivery: Molecular Imprinting of Biologically Significant Molecules", Advanced Drug Delivery Reviews, vol. 56 (2004), pp. 1599-1620. Jul. 28, 2004.

(Continued)

*Primary Examiner* — Robert M Kelly
(74) *Attorney, Agent, or Firm* — McKee, Voorhees & Sease, PLC

(57) ABSTRACT

A system for delivering a therapeutic dose of a drug is disclosed. The system includes a delivery medium with therapeutic units attached thereto. The delivery medium is preferably a polymeric hydrogel matrix that has therapeutic units incorporated therein or metal nanoparticles with therapeutic units complexed thereto. The therapeutic units include nucleic acid moieties. The nucleic acid moieties preferably include strands of nucleic acid and drug moieties complexed with the strands of nucleic acid. Where the system includes a polymeric hydrogel matrix, an active drug is controllably released from the polymer hydrogel matrix to provide a therapeutic dose to a biological system or biological tissue. The active drug is controllably released from the hydrogel matrix by altering the environment the hydrogel matrix, or by enzymatic cleavage of the nucleic acid moieties or by a combination thereof.

9 Claims, 9 Drawing Sheets

(56) References Cited

OTHER PUBLICATIONS

Hiratani, Haruyuki, et al., "The Nature of Backbone Monomers Determines the Performance of Imprinted Soft Contact Lenses as Timolol Drug Delivery Systems", Biomaterials, vol. 25 (2004), pp. 1105-1113. Jul. 22, 2003.

Hiratani, Haruyuki, et al., "Timolol Uptake and Release by Imprinted Soft Contact Lenses Made of N,N-diethylacrylamide and Methacrylic Acid", Journal of Controlled Release, vol. 83 (2002), pp. 223-230. Jul. 24, 2002.

Kulbachinskiy, A. V., "Methods for Selection of Aptamers to Protein Targets", Biochemistry (Moscow), vol. 72, No. 13 (2007), pp. 1505-1518. Feb. 9, 2006.

Saettone, Marco Fabrizio, "Progress and Problems in Ophthalmic Drug Delivery", Business Briefing: Pharmatech (2002). Jan. 31, 2002.

Schoenwald, Ronald D., "Ocular Pharmacokinetics", Textbook of Ocular Pharmacology, Chapter 9, Lippincott-Raven Publishers, Philadelphia, (1997), pp. 119-138. Jan. 31, 1997.

Taton, T. Andrew, et al., "Scanometric DNA Array Detection With Nanoparticle Probes", Science, vol. 289, Sep. 8, 2000, pp. 1757-1760. Sep. 8, 2000.

Elghanian, Robert, et al., "Selective Colorimetric Detection of Polynucleotides Based on the Distance-Dependent Optical Properties of Gold Nanoparticles", Science, vol. 277, pp. 1078-1081. Aug. 22, 1997.

Venkatesh, S., et al., "A Biomimetic Approach of Recognitive Contact Lenses for Tailored Loading and Release of Antihistamines to Treat Allergic Rhinoconjunctivitis", Dept. Chemical Engineering, Auburn Univ., Auburn AL, USA 36849, p. 25. Jan. 31, 2006.

Venkatesh, S., et al., A Biomimetic Approach Towards the Formation of Therapeutic Contact Lenses, Dept of Chemical Engineering, Auburn Univ., Auburn AL, USA, p. 24. Jan. 31, 2006.

Venkatesh, S., et al., "Applications of Biomimetic Systems in Drug Delivery", Expert. Opin. Drug Deliv., vol. 2, No. 5, pp. 1085-1096. Jan. 31, 2005.

Venkatesh, S., et al., "Biomimetic Recognitive Polymer Networks for Ocular Delivery of Anti-Histamines", Mater. Res. Soc. Symp. Proc., vol. 897E, 6 pgs. Jan. 31, 2005.

Venkatesh, S., et al., "Ophthalmic Antihistamine Delivery Via Recognitive Contact Lenses for Allergic Relief", Dept. Chem. Engineering, Auburn Univ., AL, USA, 6 pgs. Jan. 31, 2006.

Venkatesh, S., et al., "Therapeutic Contact Lenses: A Biomimetic Approach Towards Ophthalmic Extended Delivery", Polymeric Materials: Science & Engineering, vol. 94, pp. 766-767. Jan. 31, 2006.

* cited by examiner

DRUG DELIVERY SYSTEM AND METHOD

CROSS-REFERENCE TO RELATED APPLICATIONS

This application is a continuation of U.S. application Ser. No. 11/985,263 filed Nov. 13, 2007, now abandoned, which claims priority under 35 U.S.C. § 119(e) of U.S. Provisional Application Ser. No. 60/937,773, titled "Drug Delivery Vehicles for On-Demand Therapeutic Release," filed Jun. 28, 2007 and U.S. Provisional Application Ser. No. 60/858,553, titled "Hypersensitive Modulating Elements for Therapeutic Delivery," filed Nov. 13, 2006, each of which are hereby incorporated by reference in their entirety.

FIELD OF THE INVENTION

The invention relates to drug delivery systems. More specifically, this invention relates to systems for and methods of controlled drug delivery using a delivery medium and nucleic acids incorporated therein.

BACKGROUND OF THE INVENTION

Routes of administration of drugs are commonly administered via topical, enteral (via the digestive tract), parenteral routes (injection or infusion). Topical generally refers to, but is not limited to epicutaneous, inhalational, intranasal, vaginal, ocular surface and ear drops. Enteral generally refers to, but is not limited to the digestive tract, oral cavity, gastric cavity, and rectal administration. Parenteral generally refers to, but is not limited to administration by injection or infusion via intravenous, intrarterial, intramuscular, subcutaneous, transdermal, transmucosal, intradermal, intrathecal, intraosseous, intracardiac, interperitoneal, intravitreal, and inhalational.

RNA is emerging as an important drug target and versatile therapeutic agent because it folds into complex 3-D structures capable of expressing many enzymatic activities and because it "digitally" interferes with the flow of genetic information from DNA to proteins. Recent studies demonstrated that RNA also constitutes an attractive material for nanotechnology because RNA molecules can be easily programmed to carry out specific functions through the incorporation of aptamers. These novel "smart" macromolecules can be selected from random pools of RNA molecules based on their ability to bind metals, small organic compounds, nucleic acids, proteins and even entire cells and to change their inherent resistance to degradation for our benefit.

Aptamers can be produced by a conceptually straightforward two-step process that involves in vitro synthesis of more than $10^{15}$ individual RNA molecules and screening them by column affinity chromatography. This approach is commonly known as in vitro selection or Systemic Evolution of Ligands by EXpotential enrichment (SELEX). Although RNA is sensitive to degradation by ribonucleases (RNases), its stability can be easily regulated by incorporation of modified nucleotides. For example, incorporation of fluorine-CTP and -UTP (Epicentre Bio-technologies) makes RNA resistant to degradation by ubiquitous RNase A.

Another group of "smart" RNA molecules, ribozymes, are able to catalyze fundamental biological processes such as the synthesis of proteins (transpeptidation), aminoacylation of tRNA molecules (esterification), and RNA cleavage (transesterification). Their discovery has changed our views of macromolecular evolution, recognizing the fact that an informational molecule can simultaneously possess enzymatic activity. Ribozymes have now been described in a number of systems from bacteria through humans. The ubiquity of catalytic RNAs has prompted intensive investigation into potential applications as well as the mechanism of catalysis. The catalytic performance of nucleic acids can be enhanced by the incorporation of additional functional groups. A number of new ribozymes was discovered using SELEX.

SUMMARY OF THE INVENTION

The present invention is directed to methods of and system for delivering a therapeutic dose of a drug. A system in accordance with the present invention includes a delivery medium with therapeutic units attached thereto. The delivery medium is any suitable delivery medium that can complex or incorporate the therapeutic units. For example, the delivery medium is a gel matrix, metal particles, a polymer film, a polymer network, a metal, a polymer particle, particulate gels, particulate networks, a polymeric dendrimer, a surface conjugated with complexes or any combination thereof. The therapeutic units include nucleic acid moieties with active drug portions that are controllably released to provide a therapeutic dose to a biological system or biological tissue.

Nucleic acid (NA) is a single or double stranded polymer or oligomer consisting of ribonucleotides, deoxyribonucleotides or their modified derivatives such as fluorinated RNA, methylated DNA, locked nucleic acids (LNA), peptide nucleic acids (PNA). The Nucleic acids used in the present invention can be selected or designed. NA strands can interact to form double strands or to direct NA strands towards the molecular target using hybridization (anti-sense mechanism).

The term "active drug" herein refers broadly to a molecular species that provides a therapeutic result when administered to a biological system or tissue. An active drug is, for example, an antibiotic, an anti-inflammatory, an antihistamine, an antiviral agent, a cancer drug, an anesthetic, a cycloplegic, a mydriatics, a lubricant agent, a hydrophilic agent, a decongestant, a vasoconstrictor, a vasodilater, an Immuno-suppressant, an immuno-modulating agent, an anti-glaucoma agent or a combination thereof. In accordance with the embodiments of the present invention, an active drug is also in a form of strands or fragments of RNA (ribonucleic acid) and/or DNA (deoxyribonucleic acid). Drug herein also refers to prodrugs, nucleic acids, glycoproteins, lipid conjugated drugs and protein-based drugs.

A drug herein also includes Pharmacologically active agents and can include anti-cancer drugs, analgesics, antipyretics, nonsteriodal anti-inflammatory drugs, steroidal anti-inflammatory drugs, anti-allergics, anti-histamines, anti-bacterial drugs, antibiotics, anti-infective drugs, antifungal drugs, statins, anti-anaemia drugs, cytotoxic drugs, anti-hypertensive drugs, cholesterol lowering medications, dermatological drugs, psychotherapeutic drugs, vitamins, minerals, dietetics, anti-adiposity drugs, carbohydrate metabolism drugs, protein metabolism drugs, thyroid drugs, antithyroid drugs, anti-macular degeneration drugs, anti-retinal degenerative disease drugs, anti-diabetic retinopathy drugs, anti-uveitis drugs, anti-glaucoma drugs, immuno-modulating agents, anti-viral agents, coenzymes and combinations thereof.

In accordance with an embodiment of the invention, a system for delivering a therapeutic dose of an active drug includes a polymeric hydrogel matrix. The polymeric hydrogel matrix has therapeutic units incorporated therein. The therapeutic units include strands of the NA. The strands of the NA or portions thereof can act as the active drug when they are released from the polymeric hydrogel matrix. In further embodiments the therapeutic units include strands of NA moieties. As used herein, "NA moieties" refers to strands of the NA that have drug moieties selectively bound to the stands of NA. In this embodiment the active drug includes the drug moiety or any portion of the NA moiety that is released from the polymeric hydrogel matrix to provide a therapeutic dose. In use, the NA moieties are preferably controllably and/or selectively cleaved and/or released from polymeric hydrogel matrix to thereby release the active drug portions. It will be clear to one skilled in the art from the discussion below that a drug delivery system of the present invention with different types of therapeutic units with, for example, more than one type of NA moiety and/or more than one type of drug moiety is within the scope of the preset invention. A drug delivery system with different types of therapeutic units is useful to provide a controlled release of multiple active drugs in different quantities and/or at different rates.

In accordance with the embodiments of the invention, a system for delivering a therapeutic dose of a drug includes metal nanoparticles. The metal nanoparticles are metal particles that have an average particle size in a range of 5 to 100 nanometers in diameter. The metal nanoparticles are formed from any suitable metal or combination of metals, but are preferably formed from a metal that is nontoxic or exhibits minimal toxicity to a biological system or tissue being treated. For example, the metal nanoparticles are formed from silver or gold. The metal nanoparticles are functionalized with therapeutic NA moieties, such as described above, and other moieties that solubilize the metal nanoparticles and/or receptor moieties that target biological tissues or molecules.

The drug delivery system of the present can take any number of forms. For example, the system can be in a pill form, a patch form or a liquid form. As used herein "patch form" includes a contact lens or any other form of a drug delivery system that administers a drug through extended contact with a biological tissue. Further details of therapeutic contact lenses are provided in the U.S. patent application Ser. No. 11/346,770, filed Feb. 3, 2006, and titled "Contact Drug Delivery System," the contents of which are hereby incorporated by reference.

In use, a drug delivery system in accordance with the present invention is taken orally, intravenously or absorbed through contact with a biological tissue. For example, the drug delivery system can be injected at or near a target tissue to be treated. Once the drug delivery system is taken, the polymeric hydrogel matrix with the therapeutic units provides a controlled release of an active drug. The controlled release of the active drug is achieved by altering an environment of the polymeric hydrogel matrix. For example, the polymeric hydrogel matrix is heated, treated with a pH modifier, treated with an ionic solution, exposed to an electric field and/or exposed to light. In this way the release of the active drug can be stopped or started. Alternatively, the release of the active drug is controlled over time at a rate that is regulated by a degradation rate of the NA moieties and the folding of the NA moieties in the therapeutic units. In a particular embodiment of the present invention, a controlled release of an active drug is achieved by treating the polymeric hydrogel matrix with an enzyme that selectively cleaves the strands of the NA moieties and, thereby, releases active drug portions of the therapeutic units.

In accordance with the embodiments of the present invention, a drug delivery system with polymeric hydrogel matrix and therapeutic units incorporated therein is formed by providing a backbone monomer, a cross-linking monomer and NA moieties, and initiating copolymerization of the backbone monomer and cross-linking monomer. The NA moieties are NA strands and/or NA strands with drug moieties complexed thereto. In accordance with an embodiment of the present invention NA strands are complexed with drug moieties prior to initiating copolymerization of the backbone monomer and cross-linking monomer, in situ with the formation of polymeric hydrogel matrix or after the polymeric hydrogel matrix is formed. The backbone functional groups in the polymeric hydrogel matrix are not required to interact with the drug, but rather provide a matrix to host the drug and control its release.

DETAILED DESCRIPTION OF A PREFERRED EMBODIMENT

Figure 1A:
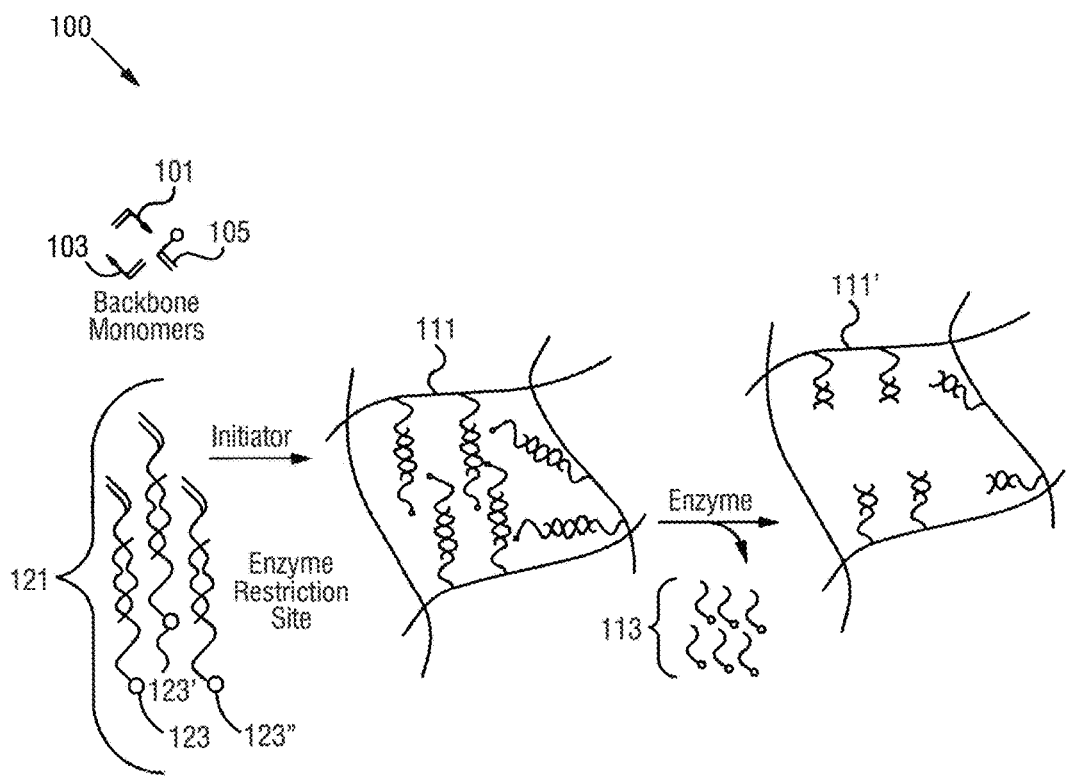
FIG. 1A is a schematic representation showing the formation of a drug delivery system with a polymeric hydrogel matrix with therapeutic units that include NA moieties, portions of which are released by enzymatic cleavage, in accordance with the embodiments of the invention.

FIG. 1A is a schematic representation 100 showing the formation of a drug delivery system 111 with a polymeric hydrogel matrix with therapeutic units 121 incorporated therein. The drug delivery system 111 is formed by providing backbone monomers 101, 103, 105, a cross-linking monomer (not shown), and therapeutic units 121, and initiating copolymerization of the backbone monomers 101, 103, 105 and the cross-linking monomer. The therapeutic units 121 are incorporated into the polymeric hydrogel matrix during the formation of the polymeric hydrogel matrix or can be incorporated into the polymeric hydrogel matrix after the polymeric hydrogel matrix is formed.

Polymeric hydrogel matrix of the present are incorporated into electrophoresis wells or used as membranes, films, etc. to add in the separation and capture of nucleic acid sequences. Electrophoresis and diffusion can both be used to construct a nucleic acid: drug complex within the gel or to remove unincorporated nucleic acid and drug moieties.

In accordance with the embodiments of the invention, a polymeric hydrogel matrix is formed from silicon-based cross-linking monomers, carbon-based or organic-based monomers, macromers or combinations thereof. Suitable cross-linking monomers include but are not limited to Polyethylene glycol (200) dimethacrylate (PEG200DMA), ethylene glycol dimethacrylate (EGDMA), tetraethyleneglycol dimethacrylate (TEGDMA), N,N'-Methylene-bis-acrylamide and polyethylene glycol (600) dimethacrylate (PEG600DMA). Suitable silicon-based cross-linking monomers include, but are not limited to, tris(trimethylsiloxy)silyl propyl methacrylate (TRIS) and hydrophilic TRIS derivatives such as tris(trimethylsiloxy)silyl propyl vinyl carbamate (TPVC), tris(trimethylsiloxy)silyl propyl glycerol methacrylate (SIGMA), tris(trimethylsiloxy)silyl propyl methacryloxyethylcarbamate (TSMC); polydimethylsiloxane (PDMS) and PDMS derivatives, such as methacrylate end-capped fluoro-grafted PDMS crosslinker, a methacrylate end-capped urethane-siloxane copolymer crosslinker, a styrene-capped siloxane polymer containing polyethylene oxide and polypropylene oxide blocks; and siloxanes containing hydrophilic grafts or amino acid residue grafts, and siloxanes containing hydrophilic blocks or containing amino acid residue grafts. The molecular structure of these monomers can be altered chemically to contain moieties that match amino acid residues or other biological molecules. In cases where the above monomers are polymerized with hydrophilic monomers, a solubilizing cosolvent may be used such as dimethylsulfoxide (DMSO), isopropanol, water, alcohol, or water/alcohol mixtures.

Preferably, crosslinkers contain more than one vinyl group in the structure or chemistry to covalently bond with multiple monomeric or oligomeric structures. Degradable crosslinkers and grafted structures degrade at a characteristic rate and include, but are not limited to poly lactic acid and polyglycolic acid macromers and derivatives, degradable thiol-ene polymers and etc.

Crosslinking monomer amounts from 0.01 to 90%, backbone monomers from 99.99% to 10% (moles backbone monomers/moles total monomers) with varying relative portions of backbone monomers (some of which may be functional and interact with the drug, nucleic acid, or both); initiator concentrations ranging from 0.1 to 30 wt %; solvent concentrations ranging from 0% to 80 wt %; monomers to therapeutic unit ratios ranging from 0.001 to 5,000, optimized to give a high therapeutic unit loading (therapeutic unit may be linked to network via covalent or non-covalent chemistry or contain an acrylate or methacrylate group and link to the network as other monomers in the polymerization reaction).

Still referring to FIG. 1, in accordance with a method of the present invention, the drug delivery system 111 is formed by making a mixture or solution that includes amounts of the therapeutic units 121, the backbone monomers 101, 103 and 105, the cross-linking monomer and a polymerization initiator in a suitable solvent or without a solvent. Suitable initiators include water and non-water soluble initiators include, but are not limited to, TEMED (N,N,N,N-Tetramethyl-Ethylenediamine) or other reaction accelerator in conjunction with ammonium persulfate, azobisisobutyronitrile (AIBN), 2,2-dimethoxy-2-phenyl acetophenone (DMPA), 1-hydroxycyclohexyl phenyl ketone (IrgacureÒ 184), 2,2-dimethoxy-1,2-diphenylethan-1-one (Irgacure 651), ammonium persulfate, iniferters such as tetraethylthiuram disulfide, or combinations thereof for living or controlled polymerization methods. The polymerization is able to be photo-initiated, thermally-initiated, redox-initiated or combinations thereof.

Examples of living or controlled polymerization include, but are not limited to living anionic or cationic polymerization, ring opening metathesis polymerization (ROMP), group transfer polymerization (GOP), living Ziegler-Natta polymerization, and free-radical polymerization (e.g., iniferter polymerization, catalytic chain transfer polymerization, stable free radical mediated polymerization (SFRP), ATRF or atom transfer radical polymerization, reversible addition fragmentation chain transfer (RAFT) polymerization, Iodine Transfer polymerization, Selenium-centered mediated polymerization, Telluride-mediated polymerization (TERP), Stibine-mediated polymerization).

The backbone monomers 101, 103 and 105 complex with the therapeutic units 121 and copolymerize with the cross-linking monomer to form the drug delivery system 111, such as described above. Alternatively, the monomers 101, 103 and 105 do not complex or weakly complex with the therapeutic units 121 and copolymerize with the cross-linking monomer to form the drug delivery system 111. Functional or reactive monomers 101 and 103 useful herein are those which possess chemical or thermodynamic compatibilities with a desired therapeutic unit 121. As used herein, the term backbone monomer includes moieties or chemical compounds that have at least one double bond group that can be incorporated into a growing polymer chain by chemical reaction and that have one end that will functionally interact with the therapeutic unit 121 through one or more of electrostatic interactions, hydrogen bonding, hydrophobic interactions, coordination complexation, and Van der Waals forces. Backbone monomers include macromers, oligomers, and polymer chains with pendent functionality and which have the capability of being crosslinked to create the recognitive hydrogel. Crosslinking monomers include chemicals with multiple double bond functionality that can be polymerized into a polymer network.

Examples of backbone monomers include, but are not limited to, 2-hydroxyethylmethacrylate (HEMA), Acrylic Acid (AA), Acrylamide (AM), N-vinyl 2-pyrrolidone (NVP), 1-vinyl-2-pyrrolidone (VP), methyl methacrylate (MMA), methacrylic acid (MAA), acetone acrylamide, 2-ethyl-2-(hydroxymethyl)-1,3-propanediol trimethacrylate, N-(1,1-dimethyl-3-oxobutyl)acrylamide, 2-ethyl-2-(hydroxymethyl)-1,3-propanediol trimethacrylate, 2,3-dihydroxypropyl methacrylate, allyl methacrylate, 3-[3,3,5,5,5-pentamethyl-1,1-bis[pentamethyldisiloxanyl)oxy] trisiloxanyl]propyl methacrylate, 3-[3,3,3-trimethyl-1,1-bis (trimethylsiloxy)disiloxanyl]propyl methacrylate (TRIS), N-(1,1-dimethyl-3-oxybutyl)acrylamide, dimethyl itaconate, 2,2,2,-trifluoro-1-(trifluoromethyl)ethyl methacrylate, 2,2,2-trifluoroethyl methacrylate, methacryloxypropylbis(trimethylsiloxy)methylsilane, methacryloxypropylpentamethyldisiloxane, (3-methacryloxy-2-hydroxypropyloxy)propylbis(trimethylsiloxy)methylsilane, 4-t-butyl-2-hydroxycyclohexyl methacrylate, dimethylacrylamide, glycerol methacrylate and diethylaminoethyl methacrylate (DEAEM).

Once the drug delivery system 111 is formed, it is fashioned into a pill, a contact lens, a patch or any other suitable form that allows it to be delivered to a biological system or biological tissue. The system 111 is formed outside or inside the body using various methods to produce films, macrofilms, microfilms, nanofilms, irregular particles and other shapes, surface coatings, particles, contact lenses with curved surfaces, etc.

Still referring to FIG. 1A, the therapeutic units 121 preferably include NA moieties 123, 123' and 123". The NA moieties include strands of NA with active drug portions 113. In use the drug delivery system 111 is delivered to a biological system or biological tissue using any suitable method. The drug delivery system 111 is then treated with an enzyme. The enzyme selectively cleaves the NA moieties 123, 123' and 123" and releases the active drug portions 113, thereby administering a therapeutic dose of the active drug portions 113 to the biological system or biological tissue.

Figure 1B:
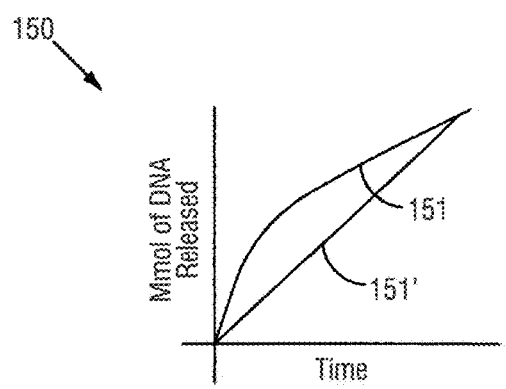
FIG. 1B illustrates a graphical representation of a controlled release profile of active drug portions of NA fragments from a drug delivery system by enzymatic cleavage within a hydrogel matrix, in accordance with the embodiments of the invention.

FIG. 1B illustrates a graphical representation 150 of a controlled release profile 151 of the active drug portions 113 from the drug delivery system 111 by enzymatic cleavage, in accordance with the embodiments of the invention. After the therapeutic dose of the active drug portion 113 is released to the biological system or biological tissue, the depleted hydrogel matrix 111' (FIG. 1A) preferably degrades within the biological system or biological tissue. The system is also controllable, such that a release profile 151" of the active drug portions 113 from the drug delivery system 111 is constant.

Figure 2A:
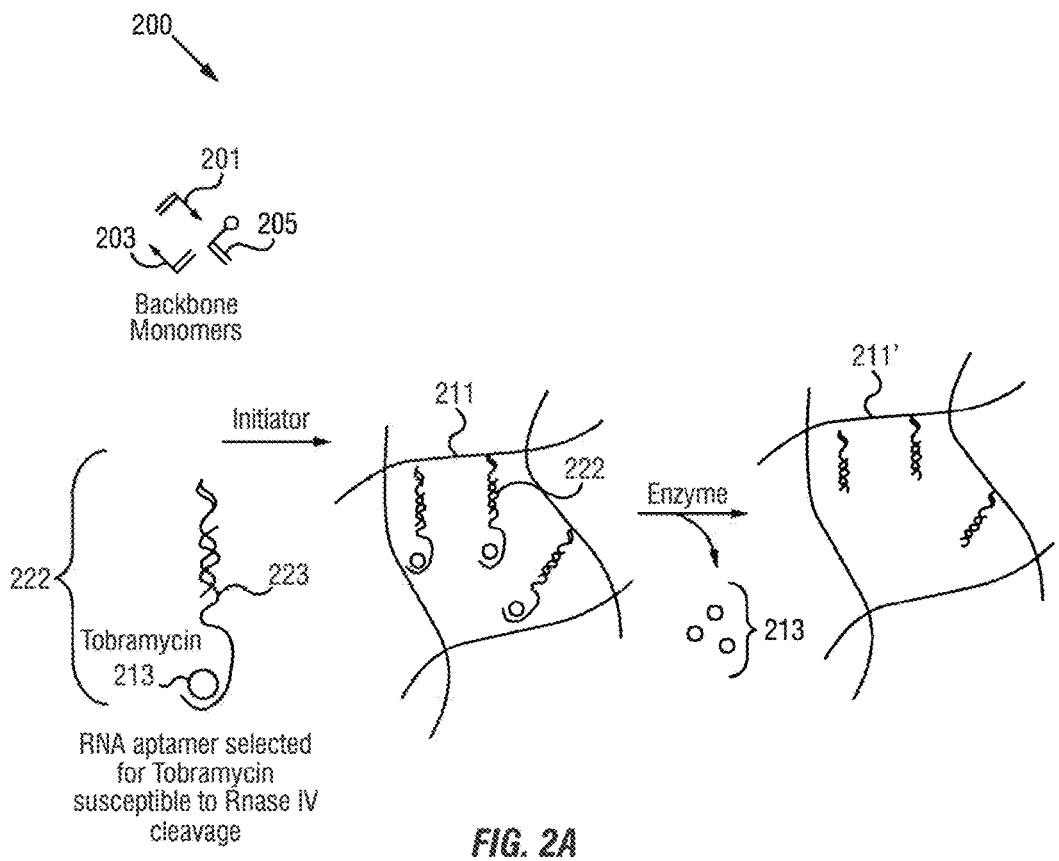
FIG. 2A is a schematic representation showing the formation of a drug delivery system with a polymeric hydrogel with therapeutic units that include strands of the NA and drug moieties complexed with strands of NA and that are released by enzymatic cleavage, in accordance with the embodiments of the invention.

FIG. 2A is a schematic representation 200 showing the formation of a drug delivery system 211, in accordance with further embodiments of the invention. The drug delivery system 211 with a polymeric hydrogel matrix further includes therapeutic units 222 incorporated into the polymeric hydrogel matrix. The drug delivery system 211 is formed by providing backbone monomers 201, 203 and 205, a cross-linking monomer (not shown) and therapeutic units 222, and initiating copolymerization of the backbone monomers 201, 203 and 205 and cross-linking monomer with a suitable initiator, such as described above.

Still referring to FIG. 2A, the therapeutic units 222 preferably include NA moieties 223. The NA moieties 223 include strands of NA such as described previously. The therapeutic units 222 further include drug moieties 213 that are complexed with the NA moieties 223. The drug moieties 213 are suitable drug molecules or a combination of drug molecules. In accordance with the embodiments of the invention, multiple drug moieties are used to administer therapeutic doses of the multiple drug moieties from a single drug delivery system 211.

Suitable drug moieties include, but are not limited to, Anti-bacterials, Anti-infectives, Anti-microbial Agents, such as anti-fungal agents (all of which generally referred to as antibiotics) such as Penicillins (including Aminopenicillins and/or penicillinas in conjunction with penicillinase inhibitor and anti-fugal agents), Cephalosporins (and the closely related cephamycins and carbapenems), Fluoroquinolones, Tetracyclines, Macrolides, Aminoglycosides. Specific examples include, but are not limited to, erythromycin, bacitracin zinc, polymyxin, polymyxin B sulfates, neomycin, gentamycin, tobramycin, gramicidin, ciprofloxacin, trimethoprim, ofloxacin, levofloxacin, gatifloxacin, moxifloxacin, norfloxacin, sodium sulfacetamide, chloramphenicol, tetracycline, azithromycin, clarithyromycin, trimethoprim sulfate and bacitracin.

Drug delivery systems of the present invention are used to deliver Non-steroidal (NSAIDs) and Steroidal Anti-inflammatory Agents (generally referred to as anti-inflammatory agents) including both COX-1 and COX-2 inhibitors. Examples include, but are not limited to, corticosteroids, medrysone, prednisolone, prednisolone acetate, prednisolone sodium phosphate, fluormetholone, dexamethasone, dexamethasone sodium phosphate, betamethasone, fluoromethasone, antazoline, fluorometholone acetate, rimexolone, loteprednol etabonate, diclofenac (diclofenac sodium), ketorolac, ketorolac tromethamine, hydrocortisone, bromfenac, flurbiprofen, antazoline and xylometazoline.

Drug delivery systems of the present invention are also used to deliver Anti-histamines, Mast cell stabilizers, and Anti-allergy Agents (generally referred to as anti-histamines). Examples include, but are not limited, cromolyn sodium, lodoxamide tromethamine, olopatadine HCl, nedocromil sodium, ketotifen fumurate, levocabastine HCL, azelastine HCL, pemirolast (pemirolast potassium), epinastine HCL, naphazoline HCL, emedastine, antazoline, pheniramine, sodium cromoglycate, N-acetyl-aspartyl glutamic acid and amlexanox.

In yet further embodiments of the invention, the drug delivery systems of the present invention are used to deliver Anti-viral Agents including, but not limited to, trifluridine and vidarabine; Anti-Cancer Therapeutics including, but not limited to, dexamethasone and 5-fluorouracil (5FU); Local Anesthetics including, but are not limited to, tetracaine, proparacaine HCL and benoxinate HCL; Cycloplegics and Mydriatics including, but not limited to, Atropine sulfate, phenylephrine HCL, Cyclopentolate HCL, scopolamine HBr, homatropine HBr, tropicamide and hydroxyamphetamine Hbr; Comfort Molecules or Molecules (generally referred as lubricating agents) to treat Keratoconjunctivitis Sicca (Dry Eye) including, but not limited to, Hyaluronic acid or hyaluronan (of varying Molecular Weight, MW), hydroxypropyl cellulose (of varying MW), gefarnate, hydroxyeicosatetranenoic acid (15-(S)-HETE), phospholipid-HETE derivatives, phoshoroylcholine or other polar lipids, carboxymethyl cellulose (of varying MW), polyethylene glycol (of varying MW), polyvinyl alcohol (of varying MW), rebamipide, pimecrolimus, ecabet sodium and hydrophilic polymers; Immuno-suppressive and Immuno-modulating Agents including, but not limited to, Cyclosporine, tacrolimus, anti-IgE and cytokine antagonists; and Anti-Glaucoma Agents including beta blockers, pilocarpine, direct-acting miotics, prostagladins, alpha adrenergic agonists, carbonic anhydrase inhibitors including, but not limited to betaxolol HCL, levobunolol HCL, metipranolol HCL, timolol maleate or hemihydrate, carteolol HCL, carbachol, pilocarpine HCL, latanoprost, bimatoprost, travoprost, brimonidine tartrate, apraclonidine HCL, brinzolamide and dorzolamide HCL; decongestants, vasodilaters vasoconstrictors including, but not limited to epinephrine and pseudoephedrine.

Still referring to FIG. 2A, in use, the drug delivery system 211 is delivered to a biological system or biological tissue using any suitable method. The drug delivery system 211 is then treated with an enzyme, a denaturing agent or any other suitable chemical that causes the complexed drug moieties 213 to be controllably released from the polymeric hydrogel matrix, to thereby administering a therapeutic dose of the drug moieties 213 to the biological system or biological tissue.

Figure 2B:
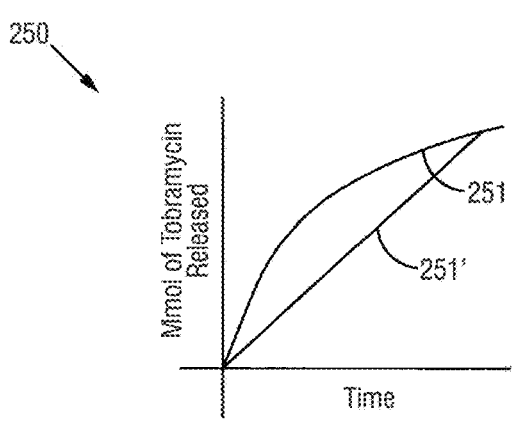
FIG. 2B illustrates a graphical representation of a controlled release profile of drug moieties from strands of NA in a hydrogel matrix, in accordance with the embodiments of the invention.

FIG. 2B illustrates a graphical representation 250 of a controlled release profile 251 of the drug moieties 213 from the drug delivery system 211 (FIG. 2A), in accordance with the embodiments of the invention. After the therapeutic dose of the drug moieties 213 is released to the biological system or biological tissue, the depleted hydrogel matrix 211' preferably degrades within the biological system or biological tissue. The system is also controllable, such that a release profile 251" of the active drug portions 213 from the drug delivery system 211 is constant It will be clear to one skilled in the art that a controlled release of the active drug portions 113 (FIG. 1A) and/or drug moieties 213 (FIG. 2A) can be achieved by altering an environment of the polymeric hydrogel matrix in any number of different ways. For example, the polymeric hydrogel matrix can be heated, treated with a pH modifier, treated with an ionic solution, exposed to light to controllably release the active drug portions 113 and/or drug moieties 213. Alternatively, the active drug portions 113 and/or drug moieties 213 are released through bio-degradation of the NA moieties within a biological system or biological tissue. Also and described previously, controlled release of the active drug portions 113 and/or drug moieties 213 can be achieved by degradation of any portion of the systems.

The release of the complexed drug moieties 213 (FIG. 2A) can be controlled through the affinity of the drug moieties 213 with the NA moieties 223. For example, a strongly complexed drug moieties 213 will be released from the system 211 at a slower rate than that of a weakly complexed drug moieties 213. In some cases where drug moieties 213 are very strongly complexed, the drug moieties 213 will only be released from the system by degradation of the NA moieties 223. If, however, drug moieties 213 are very weakly complexed, the drug moieties 213 will be released from the system 211 based primarily on the concentration gradient of the drug moieties 213.

Also, NA aptamer-drug complexes in accordance with the embodiment of the invention are noncovalently linked and/or dispersed within a gel structure. Release of therapeutic can be controlled by the macromolecular architecture. For instance, a tight crosslinking structure will lead to an increased transport of therapeutic from the structure but significantly deter the NA sequences depending on the size of these structures. The affinity of the NA for the therapeutic along with the structure of the gel will determine the release rate.

Figure 3:
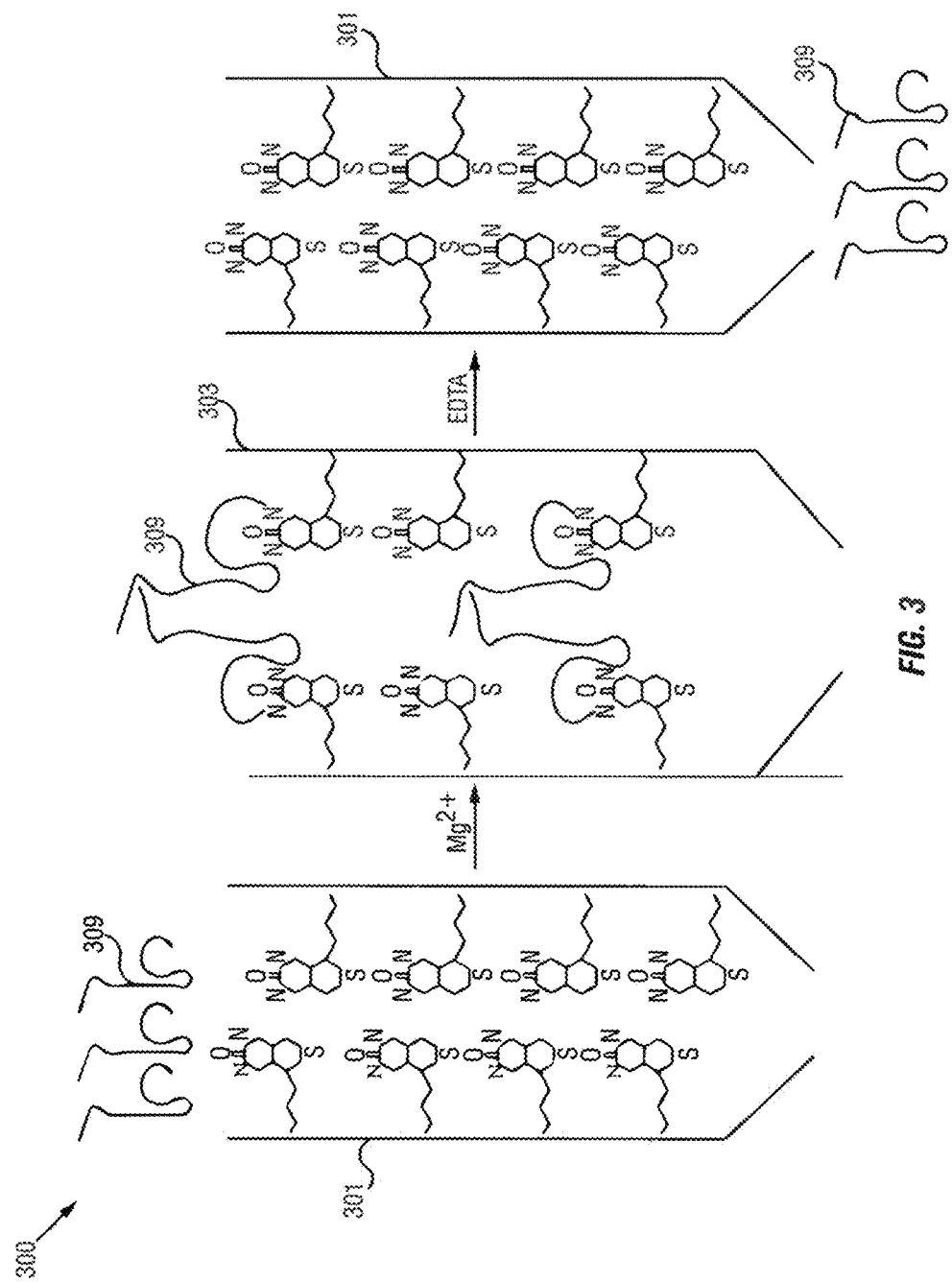
FIG. 3 is a schematic representation showing the formation of a drug delivery system with a polymeric hydrogel and therapeutic units that include strands of the NA that are released by altering the environment of the polymeric hydrogel, in accordance with the embodiments of the invention.

FIG. 3 is a schematic representation 300 showing the formation of a drug delivery system 303 with a polymeric hydrogel matrix 301 and therapeutic units 309 that include strands of NA. The therapeutic units 309 are incorporated into the polymeric hydrogel matrix 301 after the polymeric hydrogel matrix 301 is formed. The therapeutic units 309 are incorporated into the polymeric hydrogel matrix 301 by treating the polymeric hydrogel matrix 301 with the therapeutic units 309 in an ionic environment to form the drug delivery system 303. The ionic environment can, for example, be a solution of magnesium ions or any other suitable solution of metal ions.

Still referring to FIG. 3, in use, the drug delivery system 303 is delivered to a biological system or biological tissue using any suitable method. The drug delivery system 303 is then treated with a chelating agent, such as ethylenediamine tetraacetate, that chelates the metal ions and, thereby, releases the therapeutic units 309 from the polymeric hydrogel matrix 301 and into the biological system or biological tissue being treated.

Figure 4A:
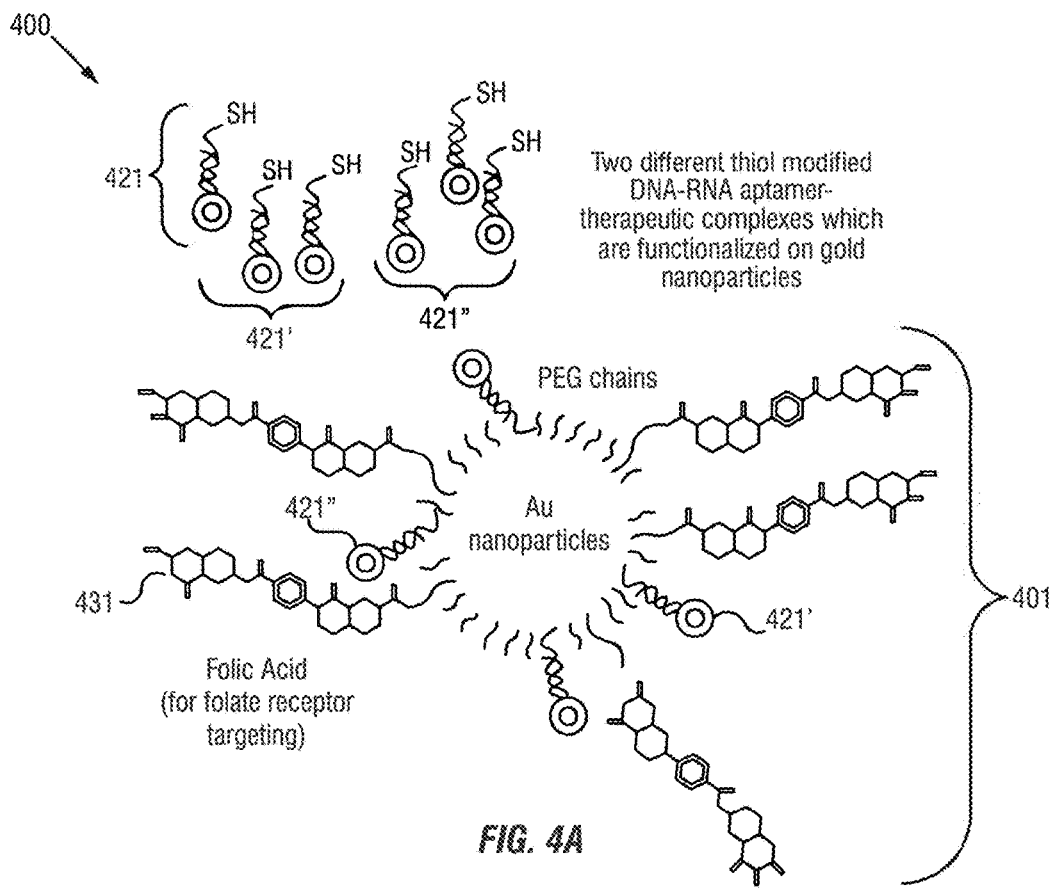
FIG. 4A is a schematic representation showing the formation of a drug delivery system with metal nanoparticles that are functionalized with receptor molecules and two different therapeutic units each including NA moieties, in accordance with the embodiments of the invention.

FIG. 4A is a schematic representation 400 showing the formation of a drug delivery system 401 with metal nanoparticles that are functionalized with receptor molecules 431 and therapeutic units 421. The receptor molecules or ligand molecules 431 are provided to target specific cells in the body. The particle surface can also be passivated using polyethylene glycol to evade immune surveillance and the reticuloendothelial system (RES) or extend circulation time (delay excretion).

The metal nanoparticles are metal particles that have an average particle size in a range of 5 to 100 nanometers in diameter and are formed from silver or gold or a combination thereof. Larger metal nanoparticles greater than 100 nanometers are considered to within the scope of the invention.

In accordance with the embodiments of this invention, the therapeutic units 421 include at least two different therapeutic units 421' and 421" each including NA moieties or NA moieties with drug moieties complexed thereto. The different therapeutic units 421' and 421" are complexed to the metal nanoparticles through any number of chemical processes. For example the different therapeutic units 421' and 421" are tailored with a thiol group that bond to a surface of the metal nanoparticles. The receptor molecules 431 are provided to solubilize the metal nanoparticles and/or target specific biological tissues.

Still referring to FIG. 4A, in use, the drug delivery system 401 is delivered to a biological system or biological tissue using any suitable method. The drug delivery system 401 or the environment of the drug delivery system 401 is then altered chemically, photo-chemically or physically, such that the different therapeutic units 421' and 421" or portions of the different therapeutic units 421' and 421" (active drug portions) are released from the metal nanoparticles and into the biological system or biological tissue being treated. Alternatively, the different therapeutic units 421' and 421" or portions of the different therapeutic units 421' and 421" are released from the metal nanoparticles through bio-degradation of the NA portions of the different therapeutic units 421' and 421" within the biological environment being treated. Release of the different therapeutic units 421' and 421" can also occur from unfolding of the RNA, degradation of the RNA, or if the affinity of the nucleic acid-drug complex optimized-release by a concentration gradient. The affinity of the nucleic acid for drug can be controlled and selected.

Figure 4B:
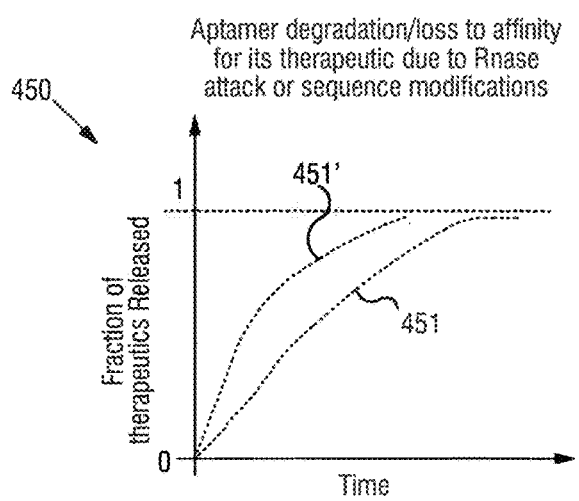
FIG. 4B illustrates a graphical representation of controlled release profiles for two different active drugs released from the drug delivery system represented in FIG. 4A, in accordance with the embodiments of the invention.

FIG. 4B illustrates a graphical representation 450 of controlled release profiles 451 and 451' of two different therapeutic units 421' and 421" or portions of the two different therapeutic units 421' and 421" as they are released from the drug delivery system 401 represented in FIG. 4A, in accordance with the embodiments of the invention. From the controlled release profiles 451 and 451' it can be seen that the different therapeutic units 421' and 421" or portions of the two different therapeutic units 421' and 421" are released at different rates. In this way a therapeutic dose of a drug cocktail is able to be administered to a biological system or biological tissue.

Figure 5:
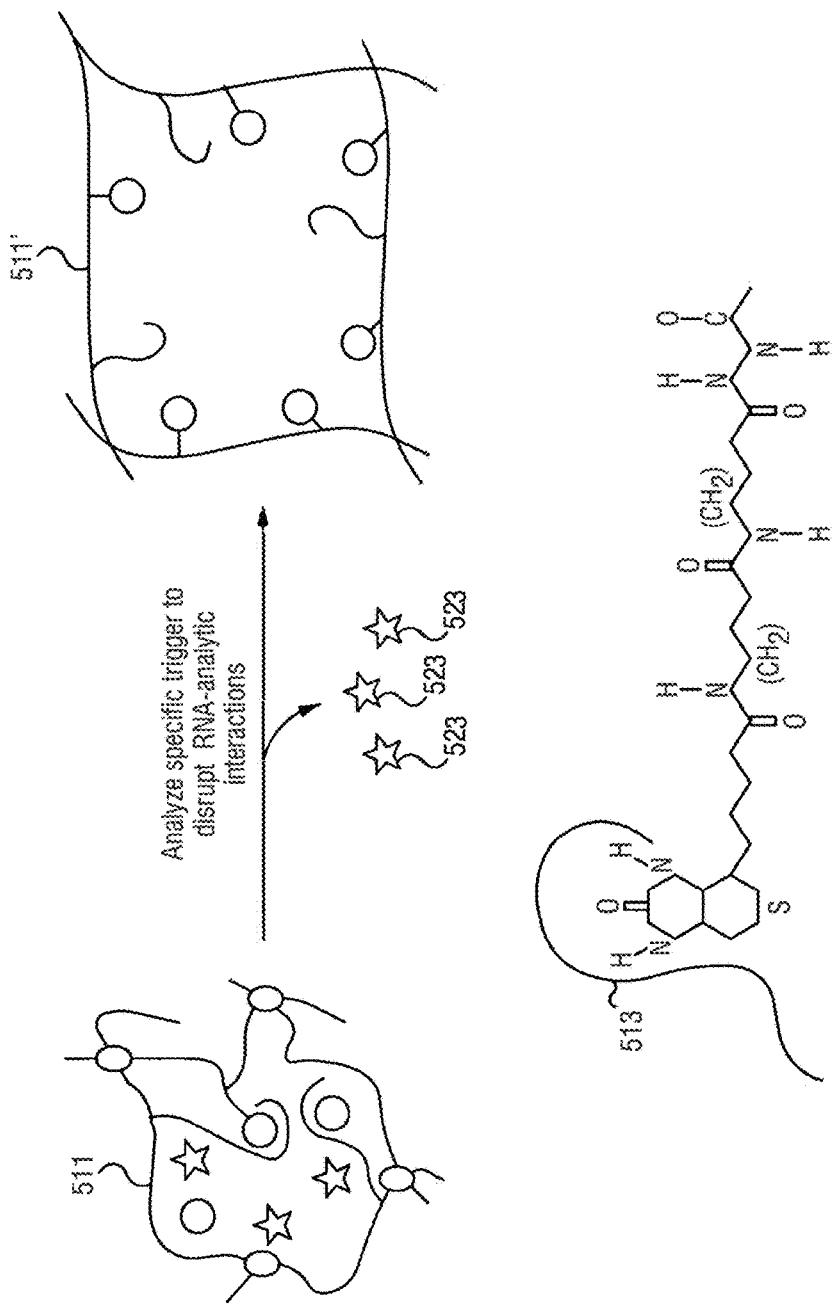
FIG. 5 shows Structure and Function of an Intelligent Biohybrid Hydrogel with RNA Crosslinks.

FIG. 5 represents a Reversible Effective Crosslinking within gel by an NA aptamer binding molecule or NA moiety 513. A conjugated or covalently attached molecule (which could be a sugar, therapeutic, biological marker, antigen, antibody, or other biologically significant moiety) to polymer chains can complex with a conjugated NA aptamer and provide reversible effective crosslinks in the gel. A dispersed therapeutic 523 in the gel can then be modulated in release. When the complex is formed, transport of drug 523 is reduced and when the complex 511 is not formed the transport of drug is significantly increased leading to on-off modulated delivery. Also, if a free molecule enters the gel that is similar to or the same as the covalently attached molecule, release of the dispersed therapeutic will be concentration dependent and triggered by the free molecule. After the drug 523 is released, the depleted polymer 511' preferably biodegrades.

A conjugated or covalently attached molecule (which could be a sugar, therapeutic, biological marker, antigen, antibody, or other biologically significant moiety) to polymer chains can complex with a conjugated NA aptamer and provide reversible effective crosslinks in the gel. A dispersed therapeutic in the gel can then be modulated in release. When the complex is formed transport of drug is reduced and when the complex is not formed or inhibited the transport of drug is significantly increased leading to on-off modulated delivery. Also, if a free molecule enters the gel that is similar to or the same as the covalently attached molecule, release of the dispersed therapeutic will be concentration dependent and triggered by the free molecule.

Figure 6A:
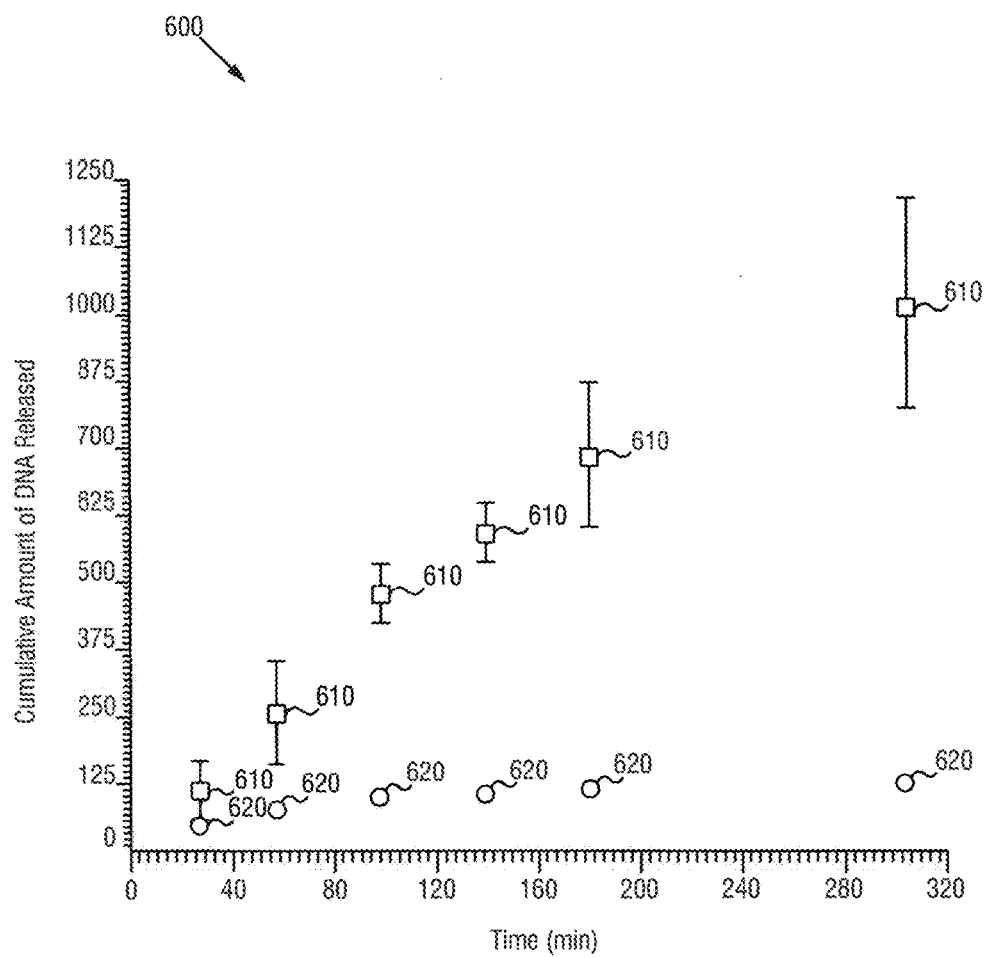
FIGS. 6A-B show Dynamic Tunable Release Profiles of DNA from Novel Biohybrid Gels by Enzymatic or Temperature Triggers.
Figure 6B:
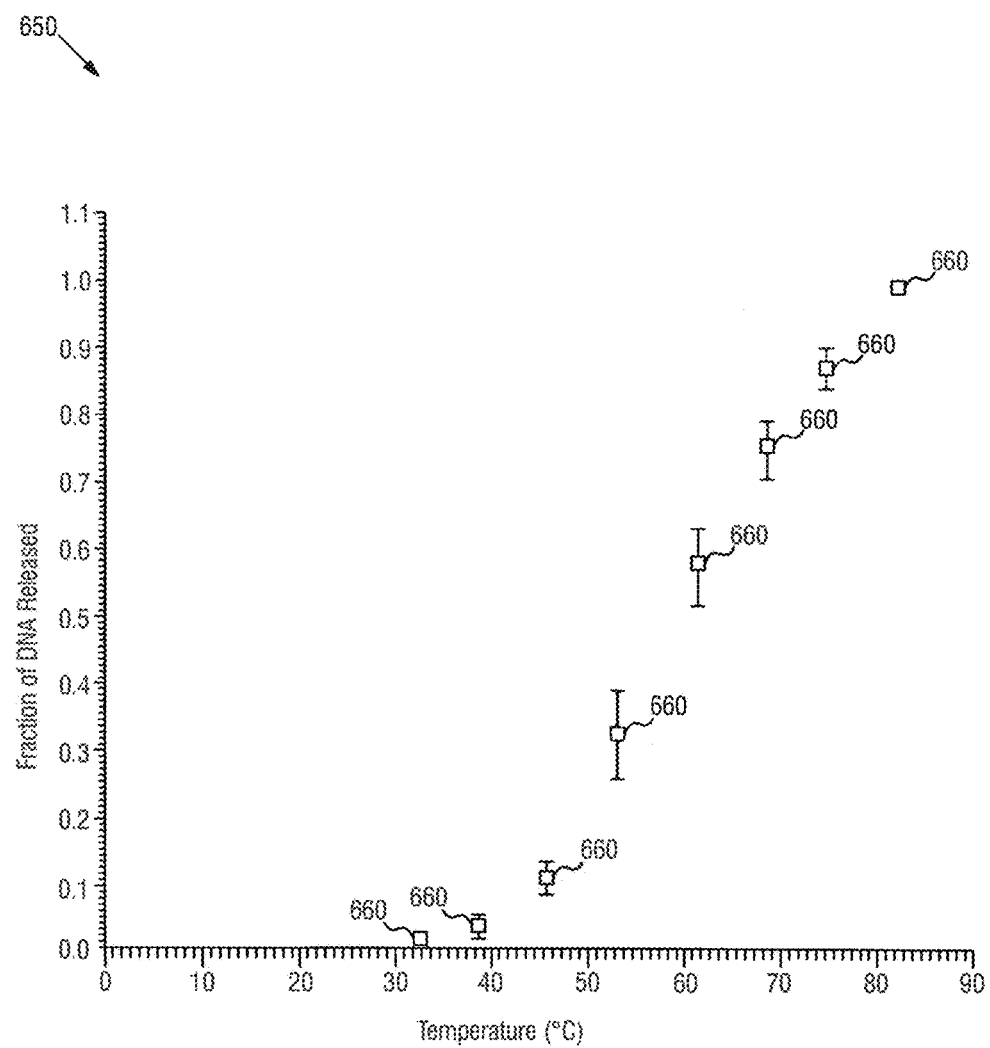

Despite entrapment in the network, the DNA helix can be readily cleaved by restriction enzyme, leading to controlled release of the cleaved DNA strands (FIG. 6A). FIG. 6A and FIG. 6B show Dynamic Tunable Release Profiles of DNA from Novel Biohybrid Gels by Enzymatic or Temperature triggers. FIG. 6A illustrates a graph 600 showing the tailored release of DNA by incubating the gels in BamHI at physiological conditions, as illustrated by the line 610, as compared to incubating in the buffer only, as illustrated by the line 620. FIG. 6B illustrates a graph 650 showing the sigmoidal temperature dependent release of DNA, as illustrated by the line 660. FIG. 6B highlights the temperature responsive release characteristics which match the theoretical melting temperature (58° C.). Since melting temperature is a direct function of G-C pairs, this will provide the opportunity to tune the release characteristics by varying the sequence. Optimization of the macromolecular structure of the network or the DNA molecules will lead to programmable release profiles.

Figure 7A:
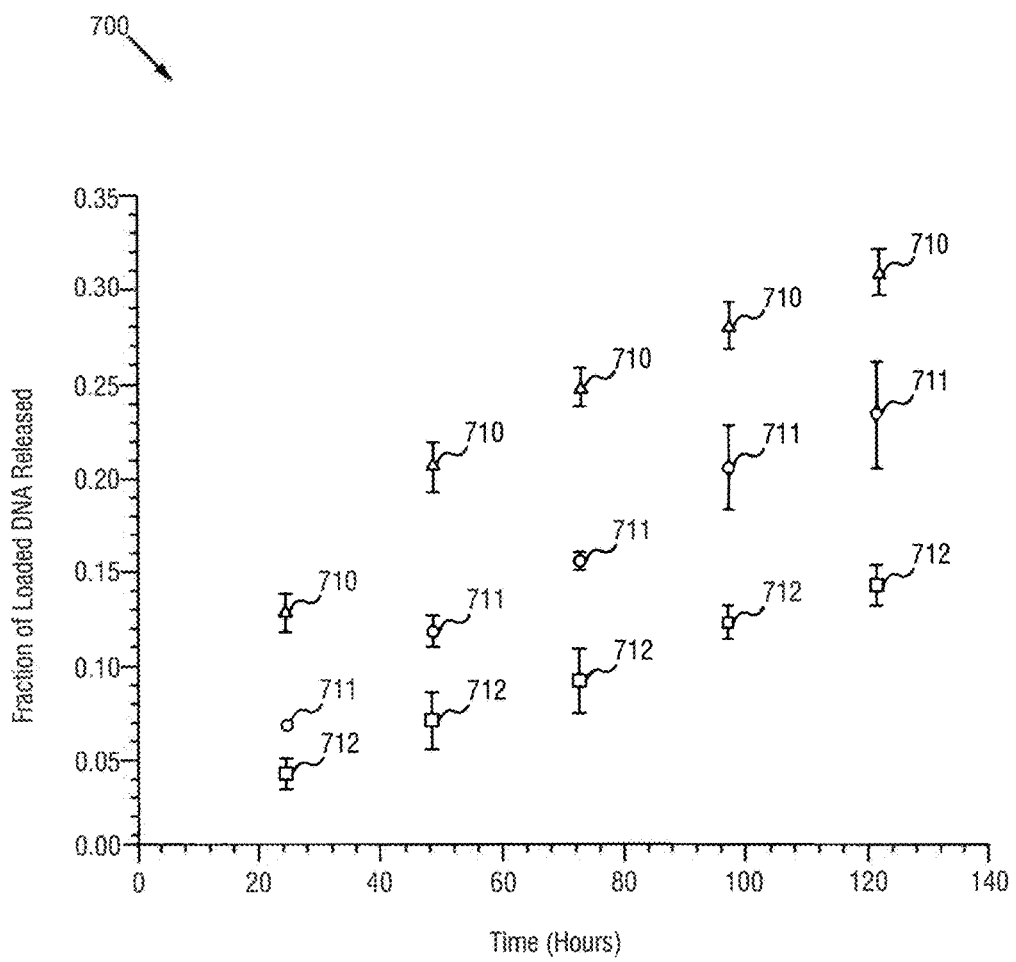
FIGS. 7A-B show Tunable Release Profiles of DNA from Biocompatible Gels by Controlling Macromolecular Architecture and Enzymatic Triggers.
Figure 7B:
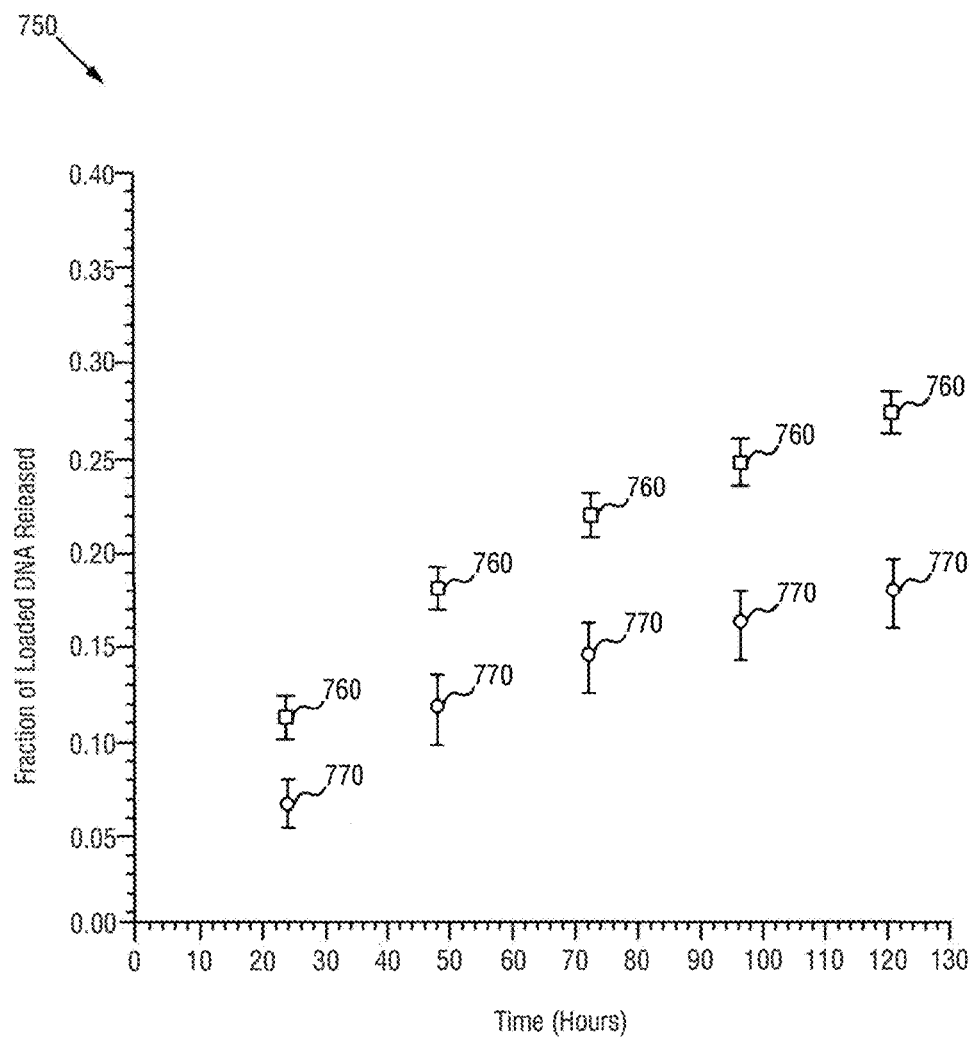

FIG. 7A and FIG. 7B show Tunable Release Profiles of DNA from Biocompatible Gels by Controlling Macromolecular Architecture and Enzymatic Triggers. FIG. 7A illustrates a graph 700 showing the tailored release of DNA by incubating the gels in DNase I at physiological conditions in biocompatible gels of varying crosslinking densities. Crosslinking densities, calculated on an acrylated DNA-free basis, was 0.15%, as illustrated by the line 710, 0.22%, as illustrated by the line 711, and 0.45%, as illustrated by the line 712. FIG. 7B illustrates a graph 750 showing the tailored release of DNA by incubating a gel of weak crosslinking density (0.15%) in DNase I at physiological conditions, as illustrated by the line 760, as compared to incubating in buffer only, as illustrated by the line 770. FIG. 7A highlights the release characteristics of biocompatible gels of varying crosslinking densities on treatment with a non-sequence specific endonuclease DNase I. FIG. 7B conclusively shows that a DNase I trigger is responsible for the cleavage of DNA covalently incorporated within a biocompatible gel.

Experimental Section

OBJECTIVE 1: The rational design, synthesis, characterization, and optimization of novel biohybrid hydrogel carriers with enhanced loading and intelligent triggered release. The model therapeutic will be an anti-Human Immunodeficiency Virus type 1 therapeutic (anti-HIV deoxyribozyme). The trigger will involve physical mechanisms (e.g., temperature, pH changes) as well as a specific biomolecular interaction, which will allow a rational tailoring and control of the therapeutic release profile.

Specific Aims:
1) Analyze the critical factors for hybridization and restriction enzyme digestion of the acrylated DNA helix;
2) Synthesize novel hydrogels with a covalently linked pendant DNA helix via redox polymerization and within the gel;
3) Characterize and optimize loading efficiency of acrylated DNA helix;
4) Analyze the in-vitro dynamic release of the cleaved DNA from the network via temperature change, pH change, a sequence specific enzymatic reaction;
5) Conduct diffusional analysis of cleaved DNA and restriction enzyme through network;
6) Synthesize networks of varying macromolecular structures (e.g., crosslinking densities) and determine the release characteristics of the cleaved DNA from biocompatible gels (e.g., synthesized from FDA-approved monomers);
7) Demonstrate physiological relevance of system with dynamic release studies of anti-HIV deoxyribozyme;
8) Perform network structural analysis via equilibrium weight and volume swelling studies.

Experiments:

In-vitro Hybridization. The 5' acrydite oligonucleotide and its complementary oligonucleotide are synthetically prepared and resuspended to 1 mM in Tris buffer, 0.5 mM EDTA, pH 8. The complementary and non-complementary oligonucleotides are radiolabeled with ?-32P ATP using 3'phosphatase-free polynucleotide kinase and purified on a denaturing 12% polyacrylamide gel Annealing of DNA strands to form double helical DNA is confirmed by the dose-dependent addition (0, 100, 200, 300 and 500 picomoles) of acrylated oligonucleotide to an aliquot of complementary oligonucleotide (5000 cpm). Each pair of oligonucleotides are heated to 90° C. for 3 minutes and directly placed on ice. Hybridization conditions are optimized in different buffers such as water and various concentrations of Tris-HCl, pH 7.5. Samples are analyzed by electrophoresis on 12% poly(acrylamide-co-bisacrylamide) non-denaturing gel. Formation of DNA duplexes are quantified using Typhoon phosphoimager and ImageQuant software (Molecular Dynamics).

In-vitro Restriction Enzyme Digestion. Digestion of the DNA helices are carried out by incubating the DNA helices with restriction enzyme and restriction enzyme buffer at 37° C. for 1 hour, as per the manufacturer's instructions. Control experiments are performed in restriction enzyme buffer only (absence of BamHI) at 37° C. for 1 hour, or on ice. Digests are analyzed by electrophoresis on non-denaturing gel. Autoradiograms are quantified using Typhoon phosphoimager and ImageQuant software.

Synthesis and Characterization of Biocompatible DNA Gels. Novel poly(acrylamide-co-N,N' methylenebisacrylamide-co-acrylated DNA), poly(acrylamide-co-polyethylene glycol 200 dimethacrylate-co-acrylated DNA), poly(2-hydrozyethyl methacrylate-co-polyethylene glycol 600 dimethacrylate-co-acrylated DNA) hydrogels of varying crosslinking densities are prepared via redox polymerization at 25° C. in the loading lanes of a non-denaturing gel. After polymerization, the unincorporated acrylated DNA and unhybridized 32P-labeled oligonucleotides are efficiently eluted by electrophoresis. The polymer gels in the loading lanes are then cut out and submerged in 10 mM Tris buffer, pH 7.5. The rest of the base gel is dried and imaged as described earlier, in order to quantify the amount of DNA incorporated into the DNA gels, and hence determine the efficiency of polymerization reaction.

In-vitro Kinetic Release of DNA Strands upon Restriction Enzyme Trigger. Release studies of 32P-labeled loaded DNA are conducted by incubating the DNA gels under physiological conditions in the presence of BamHI and BamHI buffer, and the release is monitored by Cerenkov counting. Control experiments are performed, by incubating the DNA gels in BamHI buffer (absence of BamHI), and by using the restriction endonuclease EcoRI, which does not recognize the BamHI recognition site. The enzymatic activity of BamHI is lowered by decreasing the pH and release will be monitored. Each experiment is performed five times and cumulative and differential DNA released versus time, normalized dynamic release profiles, and drug diffusion coefficient will be calculated by using Fick's Law with a diffusion coefficient that is dependent on position via one-dimensional planar solute release from the gel.

In-vitro Kinetic Release of DNA Strands upon Deoxynuclease I Trigger. Release studies of 32P-labeled loaded DNA are conducted by incubating the DNA gels under physiological conditions in the presence of DNase I (which is a non-specific endonuclease), and the release is monitored by Cerenkov counting. Control experiments are performed, by incubating the DNA gels in DNase I buffer (absence of DNaseI). The effect of the macromolecular architecture the diffusion of DNA strands from the gel to give tunable release profiles are investigated by conducting release studies in gels of varying crosslinking densities. Each experiment is performed five times and cumulative and differential DNA released versus time, normalized dynamic release profiles, and drug diffusion coefficient will be calculated by using Fick's Law with a diffusion coefficient that is dependent on position via one-dimensional planar solute release from the gel.

In-vitro Kinetic Release of DNA Strands upon Temperature Ramp Temperature-responsive release of melted DNA strands are investigated between 30° C. and 85° C. Each experiment is performed five times and cumulative and differential DNA released versus time, normalized dynamic release profiles, and drug diffusion coefficient will be calculated by using Fick's Law with a diffusion coefficient that is dependent on position via one-dimensional planar solute release from the gel.

Physiological validation of the platform: Downregulation of HIV-1 Tat/Rev mRNA. The physiological relevance of the platform in context of clinical medicine is demonstrated by following similar steps to release an anti-HIV deoxyribozyme. The double stranded helix substrate is redesigned to include a catalytic unit of a DNA enzyme that can bind to and cleave HIV-1 TAT/Rev mRNA, the coding sequence for Tat and Rev proteins, along with the BamHI recognition site. As Tat and Rev represent two essential proteins of human immunodeficiency virus type 1 (HIV-1), mRNAs encoding these proteins constitute frequent targets for DNA- and RNA-based gene therapy. Treatment of the DNA gels with BamHI results in the cleavage of the anti-HIV deoxyribozyme from the gel, and downregulation of the Tat mRNA by the mechanism stated above. The HIV aptamer is synthesized in vitro using synthetic DNA templates under the control of promoters specific to T7 RNA polymerase. The aptamer is then radiolabeled using [5'-32P]pCp and T4 RNA ligase and purified on a 12% poly(acrylamide-co-bisacrylamide) non-denaturing gel. 3'-end labeled HIV aptamer is incubated along with the DNA gels and BamHI under physiological conditions, and the cleaved RNA fragments are analyzed by electrophoresis on a denaturing gel. Autoradiograms are quantified using Typhoon phosphoimager and ImageQuant software.

Physiological validation of the platform: Downregulation of miRNA for Age-Related Macular Degeneration. The physiological relevance of this platform in the context of developmental biology and clinical intervention are demonstrated by following similar steps to release an anti-miRNA ribozyme. The double stranded helix substrate includes a siRNA construct which targets and interferes with the functioning of the vascular endothelial growth factor receptor (VEGFR). Treatment of the DNA gels with BamHI results in the cleavage of the siRNA from the gel, and downregulation of the VEGFR mRNA. The VEGFR mRNA is synthesized in vitro using synthetic DNA templates under the control of promoters specific to T7 RNA polymerase. The aptamer is then radiolabeled using [5'-32P]pCp and T4 RNA ligase and purified on a 12% poly(acrylamide-co-bisacrylamide) non-denaturing gel. 3'-end labeled VEGFR aptamer is incubated along with the DNA gels and BamHI under physiological conditions, and the cleaved RNA fragments are analyzed by electrophoresis on a denaturing gel. Autoradiograms are quantified using Typhoon phosphoimager and ImageQuant software.

Kinetic Diffusion Studies in DNA Gels. Permeation studies are conducted using Valia-Chen diffusion cells consisting of donor and acceptor reservoirs with temperature control at 37° C. Each gel is pre-swollen in Tris buffer until equilibrium and placed between the two half diffusion cells. The transport of restriction endonuclease/cleaved fragments is determined via MALDI spectrophotomer. Permeability coefficients, partition coefficients, and diffusion coefficients are calculated. Comparison of the relative rates of diffusion between the influx of BamHI and the exodus of the cleaved fragments will yield information regarding the rate limiting steps of the reactive/diffusion process.

Structural Analysis. Equilibrium weight and volume swelling studies are conducted using conventional methods to calculate polymer fractional content, gel structural properties such as molecular weight between crosslinks, and correlation length (e.g., mesh size of the gel).

OBJECTIVE 2: The rational design, synthesis, characterization, and optimization of novel biohybrid hydrogel carriers which exhibit modulatory, on-off, release of a therapeutic via reversible aptamer-analyte crosslinking.

Specific Aims:
1) Perform in-vitro transcription and purification of a biotin-specific aptamer and characterize via equilibrium and kinetic binding isotherms;
2) Synthesize novel recognitive RNA-based hydrogels using aptamer and bioconjugate chemistry;
3) Elucidate the associated mesh size changes and swelling transitions via metal ion/chelating agent switching;
4) Perform dynamic release kinetics of a fluorescent molecule from the hydrogel carrier.

Experiments:
In-vitro Transcription and Purification of an Analyte Specific Aptamer. Biotin-binding RNA pseudoknots are synthesized in vitro using synthetic DNA templates under the control of promoters specific to T7 RNA polymerase. Large quantities of DNA are generated using the Klenow fragment of DNA Polymerase I. Integrity of the transcripts are examined by denaturing polyacrylamide gel electrophoresis. Biotin binding pseudoknots are optimized for binding efficiency using SELEX. Pseudoknots are radiolabeled using [5'-32P]pCp and T4 RNA ligase and purified on a 12% poly (acrylamide-co-bisacrylamide) non-denaturing gel. Modified nucleotides are co-transcriptionally incorporated into RNA pseudoknots to render them resistant against ribonucleases and then selected for binding via affinity chromatography. For example, by modulating incorporation of fluorine-pyrimidine nucleotides (Epicentre biotechnologies) small RNAs resilient against degradation by ubiquitous RNAse A, can be produced. Protection from other RNases is achieved by posttranscriptional modification of accessible nucleotides with nucleotide specific reagents (kethoxal, DMS, DEPC).

Affinity Elution Studies. Binding properties of RNA aptamers are monitored using modified Sepharoses. Columns are equilibrated with Biotin Binding Buffer (20 mM HEPES, 100 mM KCl, 15 mM MgCl2). Loading the column with samples or magnesium/EDTA buffers is followed by spinning at 1000 rpm for 20 seconds.

Synthesis of Novel Recognitive RNA based Hydrogels using Aptamer and Bioconjugate Chemistry. Poly(acrylic acid-g-RNA-g-biotin) networks are prepared from poly (acrylic acid) chains of high monodispersity. Grafting of RNA and modified biotin amines to the matrix occur via commercially available cross-linking reagents (Maleimide chemistry-EDC, oxen chemistry). Hydrogels are assembled in polystyrene molds of precise dimensions.

Elucidation of Mesh Size Changes/Swelling Transitions via Metal Ion/Chelating Agent Switching. Observable macroscopic volume transitions are induced by metal ion/chelating agent switching, which are observed under an optical microscope. Gels are placed in known of volume of Tris buffer and the concentration of a FTIC Dextran (model drug) versus time at 37° C. will be used to determine modulatory release kinetics.

The present invention has been described in terms of specific embodiments incorporating details to facilitate the understanding of the principles of construction and operation of the invention. Such references herein to specific embodiments and details thereof are not intended to limit the scope of the claims appended hereto. It will be apparent to those skilled in the art that modifications can be made in the embodiments chosen for illustration without departing from the spirit and scope of the invention. Specifically, it will be apparent to one of ordinary skill in the art that the device of the present invention can be implemented in several different ways and the apparatus disclosed above is only illustrative of the preferred embodiment of the invention and is in no way a limitation.

What is claimed is:

1. A system for delivering a therapeutic dose of an active drug, the system comprising a delivery medium with therapeutic units, wherein the therapeutic units include strands of a nucleic acid, wherein the therapeutic units comprise one or more active drugs within the strands of the nucleic acid, wherein the strands of the nucleic acid comprise aptamers; wherein the strands of nucleic acids are a variety of lengths; wherein the system provides a controlled release and loading of said active drug; wherein the active drugs are small organic compounds; wherein the aptamers are selected based on their ability to bind the small organic compounds; and wherein the delivery medium comprises metal nanoparticles with said strands of the nucleic acid attached thereto.

2. The system of claim 1, wherein the delivery medium includes one or more of a gel matrix, a polymer film, a polymer network, metal surface, polymer particles, particulate gels, particulate networks, a polymeric dendrimer and a surface conjugated with complexes.

3. The system of claim 1, wherein said nucleic acid strands are double stranded DNA.

4. The system of claim 1, wherein the metal nanoparticles are silver or gold nanoparticles.

5. The system of claim 1, wherein the therapeutic units comprise one or more active drugs.

6. The system of claim 5, wherein the active drugs are anti-cancer drugs.

7. The system of claim 1, wherein the aptamer binds to a protein expressed by a target cell.

8. The system of claim 7, wherein said target cell is a cancer cell.

9. The system of claim 1, wherein said controlled release is a constant release of said active drugs.

* * * * *